(12) United States Patent
Kondis et al.

(10) Patent No.: US 10,456,240 B2
(45) Date of Patent: Oct. 29, 2019

(54) PATIENT INTERFACE FOR LIGHT ADJUSTABLE INTRAOCULAR LENS IRRADIATION SYSTEM

(71) Applicant: RxSight, Inc., Aliso Viejo, CA (US)

(72) Inventors: John Kondis, Irvine, CA (US); Ilya Goldshleger, Ladera Ranch, CA (US)

(73) Assignee: RxSight, Inc., Aliso Viejo, CA (US)

( * ) Notice: Subject to any disclaimer, the term of this patent is extended or adjusted under 35 U.S.C. 154(b) by 113 days.

(21) Appl. No.: 15/822,099

(22) Filed: Nov. 24, 2017

(65) Prior Publication Data

US 2019/0159889 A1 May 30, 2019

(51) Int. Cl.
| | |
|---|---|
| *A61F 2/16* | (2006.01) |
| *B29D 11/00* | (2006.01) |
| *A61F 9/00* | (2006.01) |
| *A61N 5/06* | (2006.01) |
| *A61N 5/067* | (2006.01) |

(52) U.S. Cl.
CPC ............... *A61F 2/16* (2013.01); *A61F 9/00* (2013.01); *A61N 5/0613* (2013.01); *A61F 2/1635* (2013.01); *A61F 2002/1699* (2015.04); *A61F 2009/0052* (2013.01); *A61F 2210/0085* (2013.01); *A61F 2250/0001* (2013.01); *A61F 2250/0004* (2013.01); *A61N 2005/067* (2013.01); *A61N 2005/0633* (2013.01); *A61N 2005/0648* (2013.01); *A61N 2005/0654* (2013.01); *A61N 2005/0661* (2013.01); *B29D 11/00461* (2013.01)

(58) Field of Classification Search
CPC .................................................. B29D 11/00461
See application file for complete search history.

(56) References Cited

U.S. PATENT DOCUMENTS

| | | | |
|---|---|---|---|
| 3,706,304 A | 12/1972 | Sisler | |
| 6,450,642 B1 | 9/2002 | Jethmalani et al. | |
| 6,905,641 B2 | 6/2005 | Platt et al. | |
| 2002/0100990 A1* | 8/2002 | Platt ...................... | A61F 2/1627 264/1.38 |
| 2010/0082017 A1* | 4/2010 | Zickler ..................... | A61F 2/16 606/4 |
| 2014/0135920 A1* | 5/2014 | Sahler ....................... | A61F 2/16 623/6.27 |
| 2014/0216468 A1* | 8/2014 | Goldshleger ........... | A61F 9/009 128/845 |
| 2017/0325675 A1 | 11/2017 | Liu et al. | |

* cited by examiner

*Primary Examiner* — David H Willse
*Assistant Examiner* — Javier G Blanco

(57) ABSTRACT

In embodiments, a light adjustable lens irradiation system for a light adjustable lens irradiation system, comprises an irradiation light source, for generating a UV light beam; an optical system, for directing the UV light beam towards a light adjustable intraocular lens, implanted into an eye of a patient; and a patient interface, coupled to the optical system, for stabilizing the eye relative to the optical system, to achieve an alignment of the light adjustable intraocular lens and the UV light beam.

10 Claims, 11 Drawing Sheets

PATIENT INTERFACE FOR LIGHT ADJUSTABLE INTRAOCULAR LENS IRRADIATION SYSTEM

TECHNICAL FIELD

This patent document is directed to irradiation systems for light adjustable lenses. In more detail, it is directed to patient interfaces for light adjustable intraocular irradiation systems.

BACKGROUND

Cataract often develops in aging eyes. The standard of care is to perform a cataract surgery by extracting the opaque natural lens, and replacing it by implanting an artificial intraocular lens into the capsular bag, thereby restoring healthy vision. However, after the surgery has been completed, intraocular lenses (IOLs) sometimes shift, or move away from the position they were surgically implanted in the capsular bag of the eye. This movement can shift the IOL focal point away from its intended location, typically on the retina, thereby leading to a deterioration of the optical performance of the IOL. Further, uncertainties in the eye's healing process, errors in measurements of the eye prior to surgery, and physician errors in the choice and the placement of the IOL can also contribute to a non-optimal surgical outcome. This deterioration or reduction of the optical performance often makes the difference between the patient needing to wear eye glasses after the surgery or not, and thus is a key factor of the post-surgical patient satisfaction.

Light adjustable intraocular lenses (LALs) offer a solution for this problem. If a patient returns to the doctor after the surgery to report dissatisfaction with the optical outcome because the LAL was misplaced, shifted, or was not the best selection, the doctor can mitigate the patient dissatisfaction by adjusting the LAL optical performance non-invasively. In detail, the doctor can perform a diagnostic process to determine the cause, nature and degree of the optical underperformance of the LAL. Then, the doctor can calculate what change of the optical characteristics of the LALs can compensate the underperformance. Finally, the doctor can perform an illumination procedure on the LAL to bring about the calculated change.

This adjustment is made possible by fabricating the LALs from photopolymerizable macromers, interspersed with a photoinitiator. When the doctor irradiates the LAL with a spatially modulated light source, typically emitting an UV light, the UV absorbing photo-initiator induces the photopolymerization of the macromers. The selected radial intensity profile of the irradiating UV light induces the polymerization with a corresponding radial profile. Photopolymerizing with a radial profile changes the shape of the LAL, and therefore changes the optical characteristics of the LAL. Thus, irradiating the LAL with an intensity profile changes the LAL to achieve the optical characteristics the doctor calculated to compensate the LAL's post-implantation underperformance. LAL systems and devices have been described extensively in the commonly owned U.S. Pat. No. 6,450,642, "Lenses capable of post-fabrication power modification" by J. Jethmalani et al., which is hereby incorporated in its entirety by reference.

FIGS. 1A-D illustrate aspects of this light adjustment procedure. FIG. 1A illustrates that when the LAL axis is aligned with the optical axis of the LAL irradiation system, then the beam intensity profile of the UV light beam is centered and aligned with the LAL. FIG. 1B illustrates that in the case of such alignment, the shape change induced in the LAL by the UV beam is aligned and centered with the LAL axis.

FIG. 1C illustrates the case when the LAL is not aligned with the LAL irradiation system, and thus the LAL axis is not aligned with the irradiation system axis. In this case the irradiating beam intensity profile of the UV light beam is not centered relative to the LAL axis. FIG. 1D illustrates that the shape change induced by the UV light beam in this misaligned LAL will be misaligned with the LAL axis. The optical characteristics and performance of the LAL with such a misaligned shape-change can be quite different from what the doctor calculated and planned. LALs with misaligned shape change typically do not achieve the compensation the doctor planned, and thus do not mitigate the patient's dissatisfaction. For this reason, aligning the LAL axis with the LAL irradiation system axis is important for the success of the lens adjustment procedure, and is a high priority for the design of the LAL irradiation system.

In today's LAL irradiation procedures, the eye, and the LAL in it, are aligned with the LAL irradiation system by the surgeon immobilizing the LAL manually. While this is an efficient approach, the alignment can be imperfect, and the slight shaking of the surgeon's hand may blur the irradiation pattern formed in the LAL. For all the above described reasons, any improvement towards better and more stable alignment between the LAL irradiation system and the LAL itself will lead to further improvements in the visual outcomes of cataract surgeries, and in patient satisfaction.

SUMMARY

In embodiments, a light adjustable lens irradiation system comprises an irradiation light source, for generating a UV light beam; an optical system, for directing the UV light beam towards a light adjustable intraocular lens, implanted into an eye of a patient; and a patient interface, coupled to the optical system, for stabilizing the eye relative to the optical system, to achieve an alignment of the light adjustable intraocular lens and the UV light beam.

DETAILED DESCRIPTION

Embodiments of the invention address the previously described medical needs. In particular, these embodiments improve the alignment of the implanted light adjustable lenses (LALs) with the LAL irradiation system.

Embodiments achieve this improved alignment by mechanically linking the patient's eye with the irradiation system, thus aligning the beam intensity profile with the LAL inside the patient's eye. The mechanical linking substantially increases the precision of the relative alignment between the LAL irradiation system, the irradiating beam, and the implanted LAL. The light adjustment procedure with the well-aligned beam brings about the planned LAL optical characteristics change more precisely, and therefore compensates the LAL underperformance more efficiently.

Figure 1B:
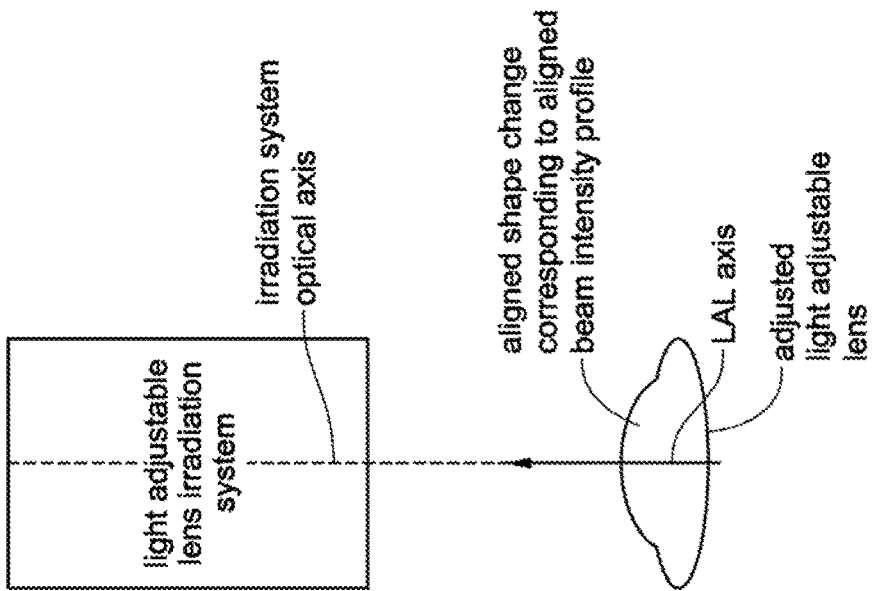
FIGS. 1A-D illustrate aligned and misaligned light adjustment processes.
Figure 1A:
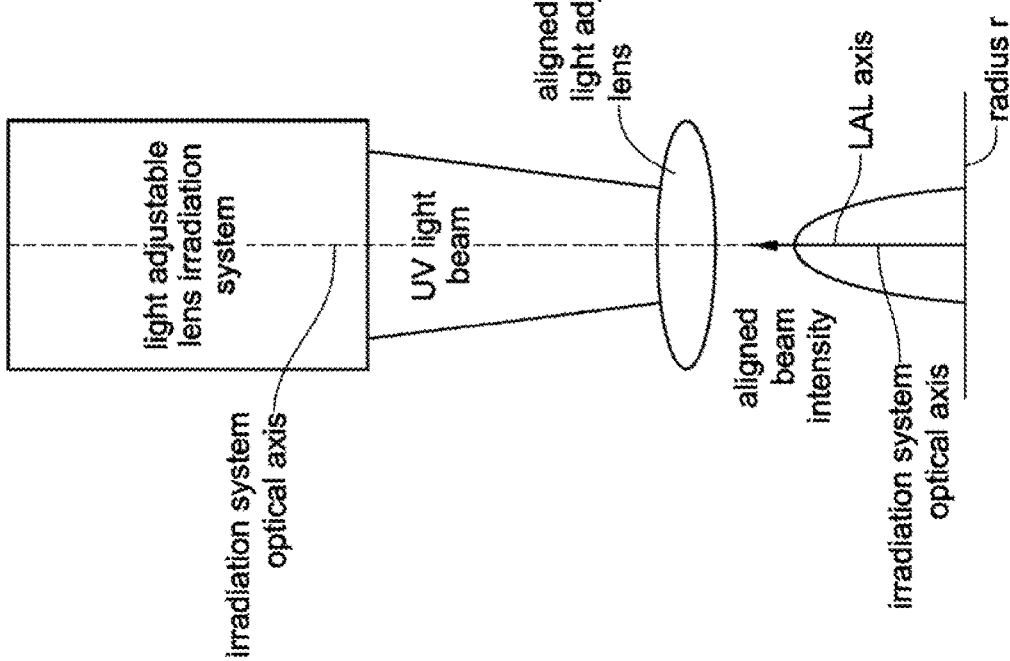
Figure 1D:
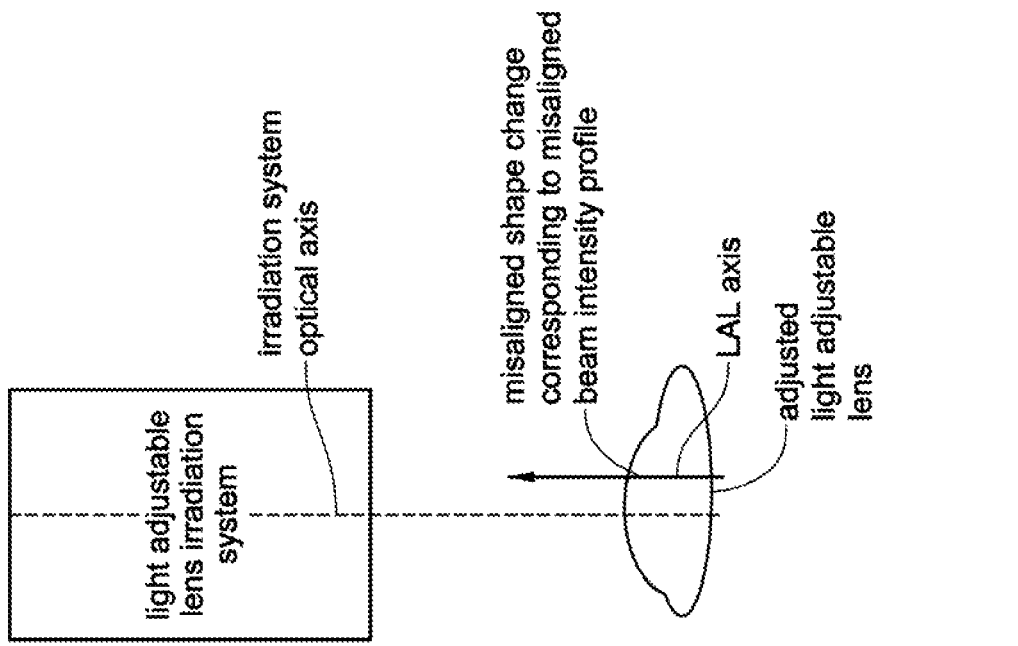
Figure 1C:
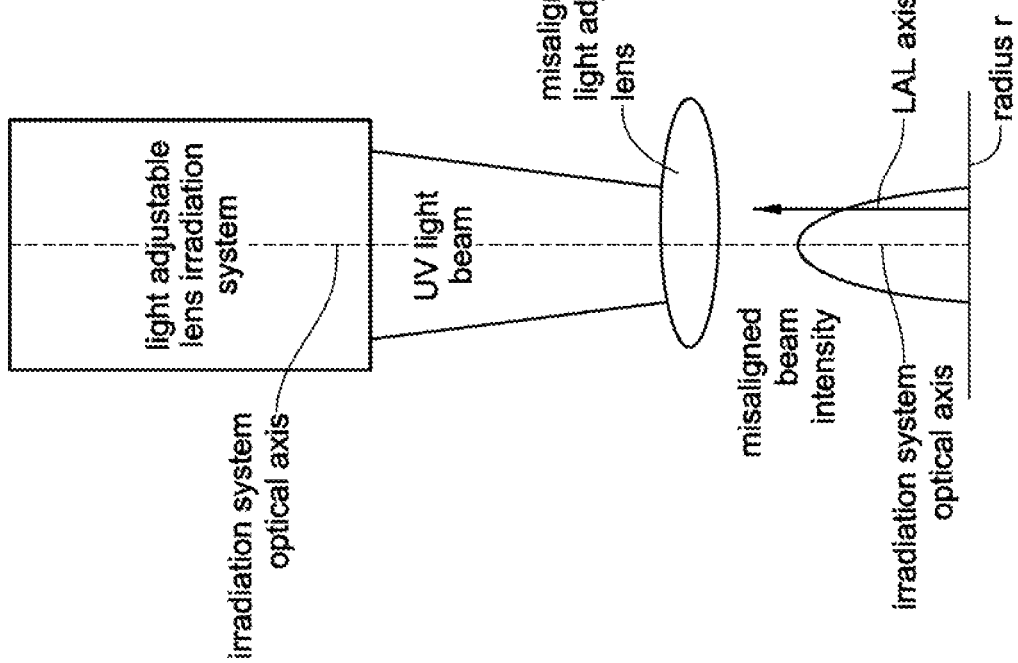
Figure 2A:
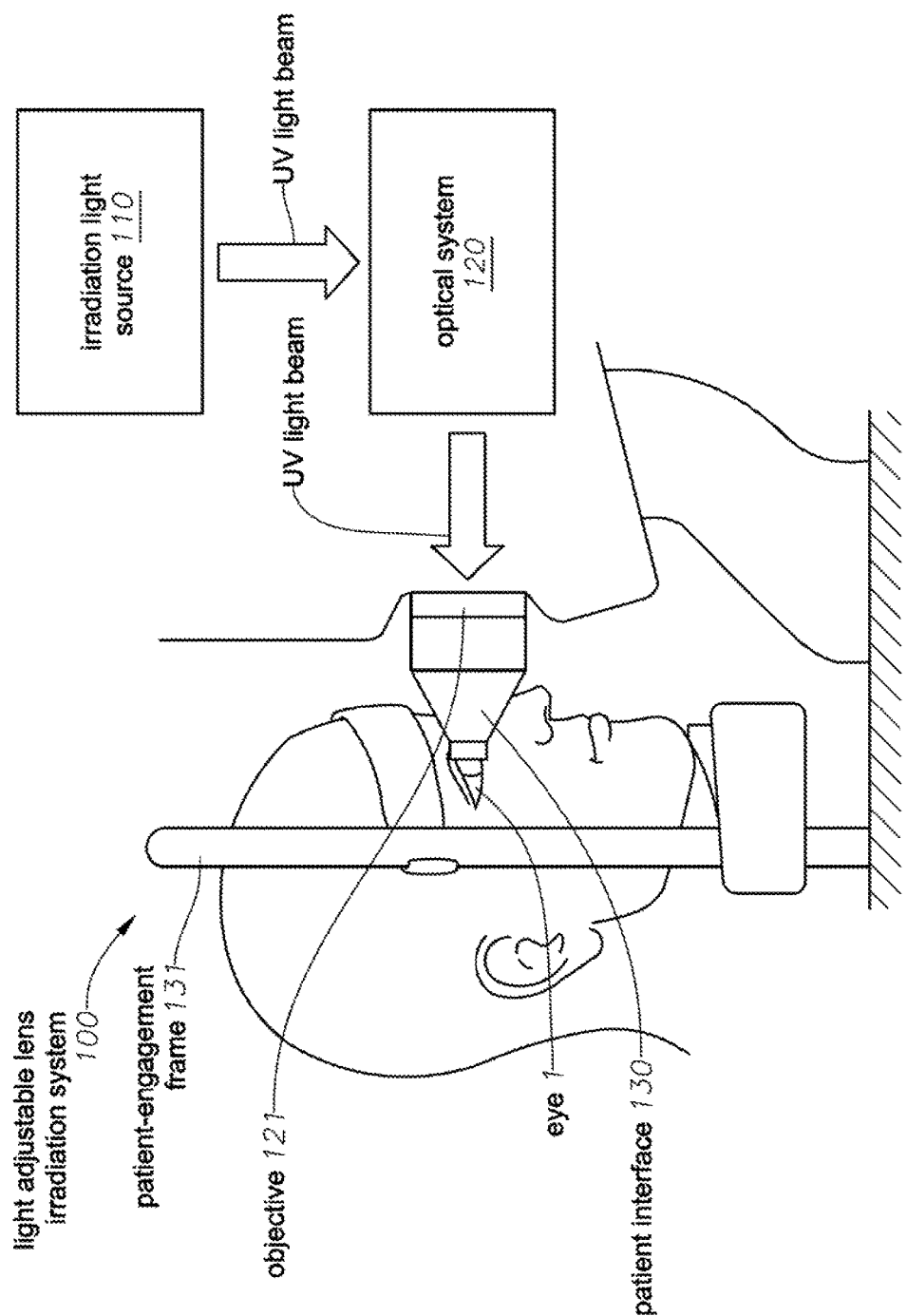
FIGS. 2A-C illustrate an embodiment of a light adjustable lens irradiation system.
Figure 2B:
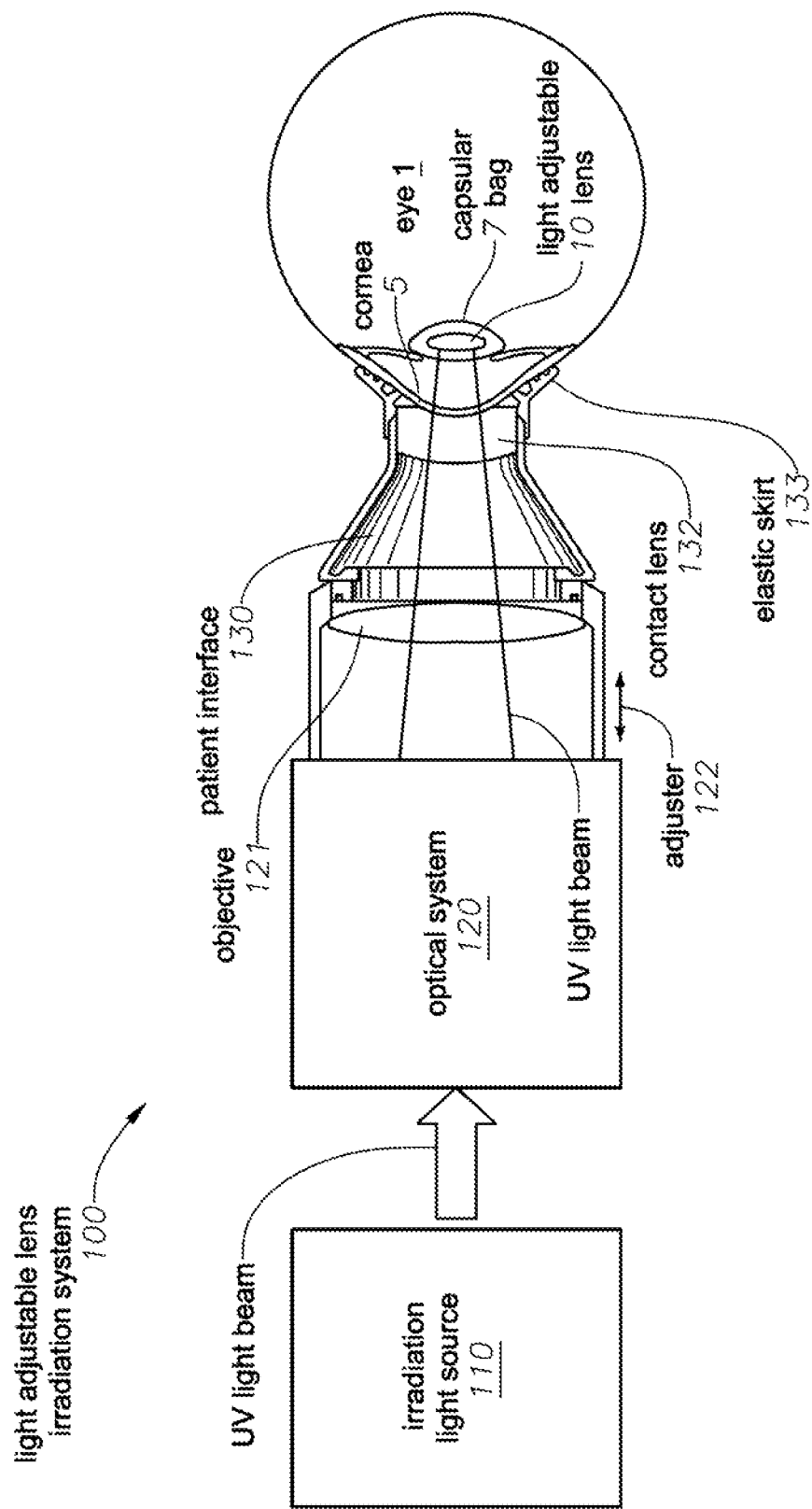
Figure 2C:
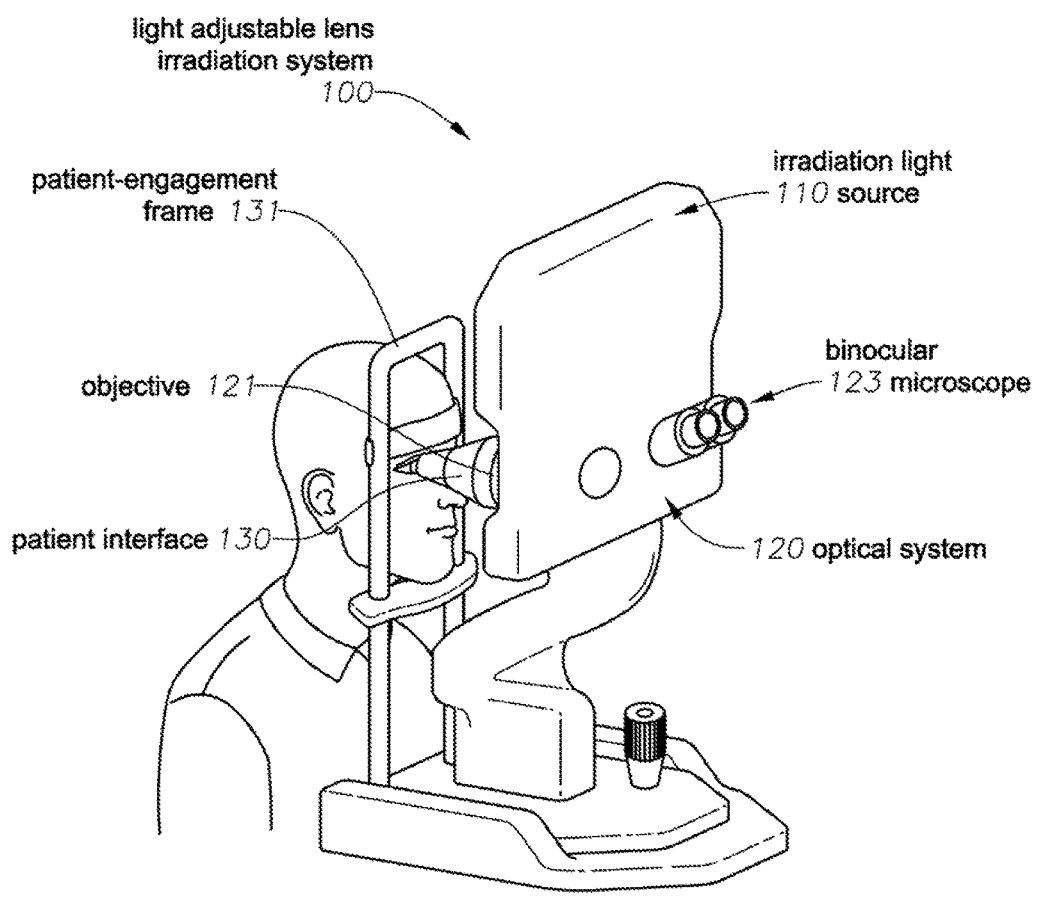

FIGS. 2A-C illustrate an embodiment of a light adjustable lens irradiation system 100 that includes an irradiation light source 110, for generating a UV light beam; an optical system 120, for directing the UV light beam towards a light adjustable intraocular lens 10, or simply light adjustable lens (LAL) 10, implanted into an eye 1 of a patient; and a patient interface 130, coupled to the optical system 120, for stabilizing the eye 1 relative to the optical system 120, to achieve an alignment of the light adjustable intraocular lens 10 and the UV light beam.

The irradiation light source 110 can emit the UV light beam in the ultraviolet wavelength range of 320-400 nm. For example, a Helium Cadmium (HeCd) laser operating at 325 nm, or a mercury (Hg) arc lamp spectrally filtered for the emission lines at 334 and 365 nm can be used as the irradiation light source 110. Other embodiments can include tripled frequency laser diode pumped solid state YAG lasers operating at 355 nm, an argon ion laser operating in the 350-360 nm range, a discharge lamp, broad-band xenon: mercury lamps operating with a spectral filter, or a UV LED, or LED array.

The optical system 120 can modulate the UV light beam to achieve a radial intensity profile by employing a digital mirror device (DMD), a spatial light modulator (SLM), such as a liquid crystal display (LCD), or a deformable mirror, among others.

In some embodiments, the optical system 120 can include an objective 121 as the distalmost optical element, facing the patient. In such embodiments, the patient interface 130 can be coupled to the objective 121 of the optical system 120.

FIG. 2A illustrates a side view of these embodiments of the light adjustable lens (LAL) irradiation system 100. Some embodiments of the LAL irradiation system 100 can include a patient-engagement frame 131. This patient-engagement frame 131 can be mounted on a rigid base shared with the optical system 120, such as a diagnostic desk. The patient can rest his/her head on a chin-rest of the patient-engagement frame 131, and press her/his forehead against a headband. The forces exerted by the chin-rest and headband can position and immobilize the patient's head relative to the optical system 120. Once the head is immobilized, the patient interface 130 can be moved forward to engage and to immobilize the eye 1 relative to the optical system 120.

FIG. 2B illustrates the contact region between the patient interface 130 and the eye 1 in some detail. The optical system 120 can include an adjuster 122 that can move the patient interface 130 to bridge the final airgap that remained between the patient interface 130 and the patient's eye 1 after it was immobilized by the patient-engagement frame 131. The doctor can adjust the adjuster 122 to move the patient interface 130 forward until it docks to a cornea 5 of the eye 1. Many other solutions can deliver this same docking function: the entire optical system 120 may be movable relative to its base, or the patient interface 130 may have a telescopic, expandable member, or the patient-engagement frame 131 can have its own adjuster 122.

The patient interface 130 can include a distalmost contact lens 132, to form a well-defined optical interface with the cornea 5 of the eye 1. The hardness of this contact lens 132 can vary, from a hard glass or PMMA lens, to a soft, hydrogel-based contact lens, similar to the disposable contact lenses placed on the cornea 5 for vision correction.

The patient interface 130 can include an elastic skirt 133 that can efficiently immobilize the eye 1 by axial mechanical pressure and lateral frictional force. The pressures and forces of the patient interface 130 can prevent the voluntary or involuntary rotation of the eye 1.

Once the head of the patient is immobilized by the patient-engagement frame 131, and the eye 1 is further immobilized, or stabilized, by the patient interface 130, the optical system 120 can direct the UV light beam onto the light adjustable lens (LAL) 10, seated in a capsular bag 7 of the eye 1, with high precision and alignment. The alignment can be fine-tuned in various ways. Once the patient interface 130 immobilized the eye 1, and thus the LAL 10 inside it, the doctor, or an automated alignment system, may adjust the targeting of the UV light beam by adjusting the targeting system of the optical system 120 laterally and possibly axially. In other embodiments, the patient interface 130 can include lateral adjusting members. In yet other embodiments, the patient-engagement frame 131 can have lateral adjustment members.

FIG. 2C illustrates the LAL irradiation system 100 from a perspective view. In some embodiments, the optical system 120 can include a binocular microscope 123, or targeting optics 123, that can assist the doctor to execute the aligning and eventual docking of the patient interface 130 with the eye 1. The binocular microscope 123 can have any combination of a wide variety of targeting and alignment systems. It can include various target illumination sources, eye-fixation lights, and targeting graphics in its optics, such as a cross hair, or targeting circles. The binocular microscope 123, or targeting optics 123, can be analog or video/digital, and can include one or more video screens or displays. It can also be a combined analog and video/digital binocular microscope 123. It can have its own optical path, or it can share the optical path of the optical system 120, at least partially. This can be achieved, e.g., by a beam splitter.

Figure 3A:
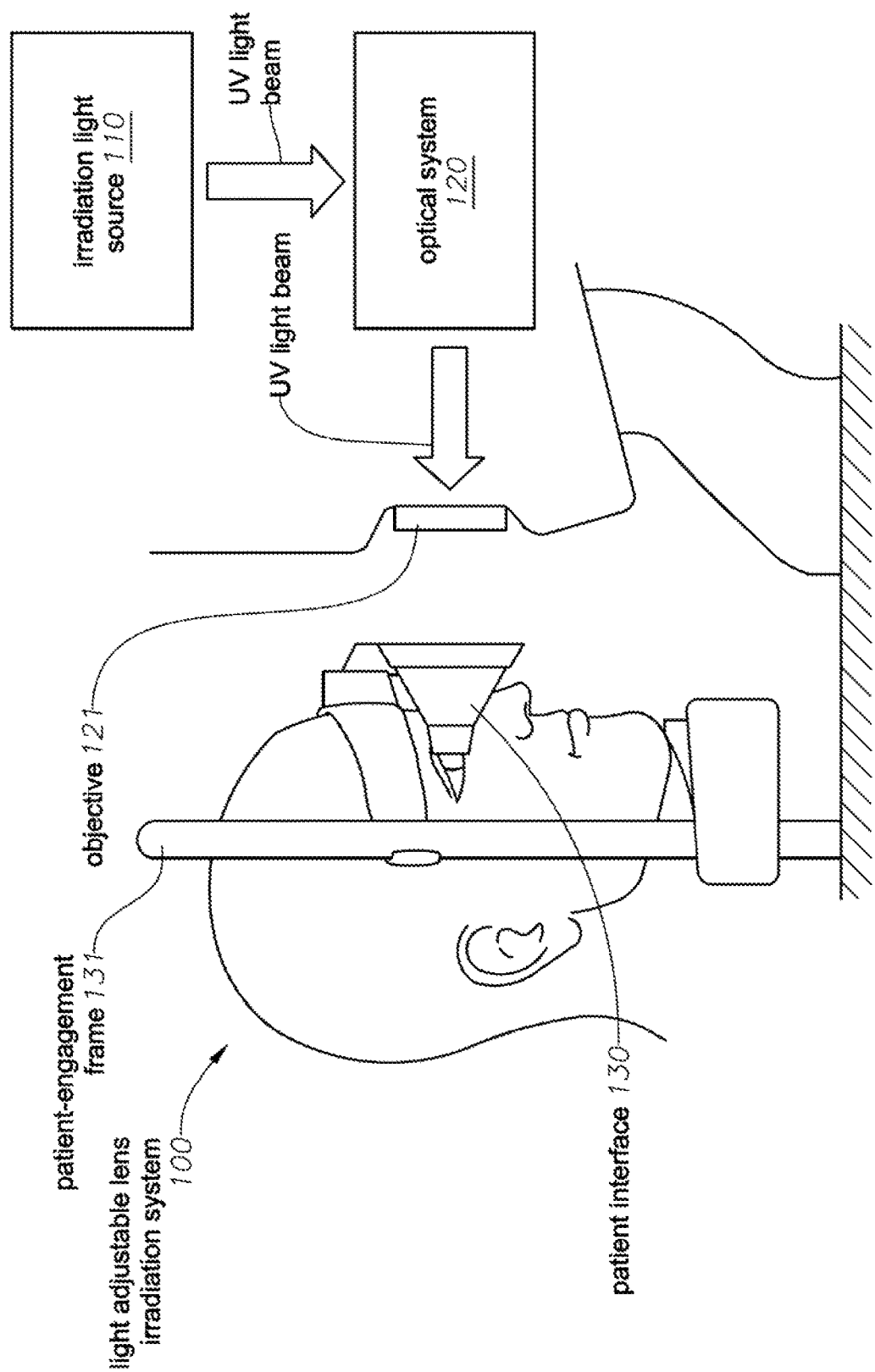
FIGS. 3A-C illustrate an embodiment of a light adjustable lens irradiation system.
Figure 3B:
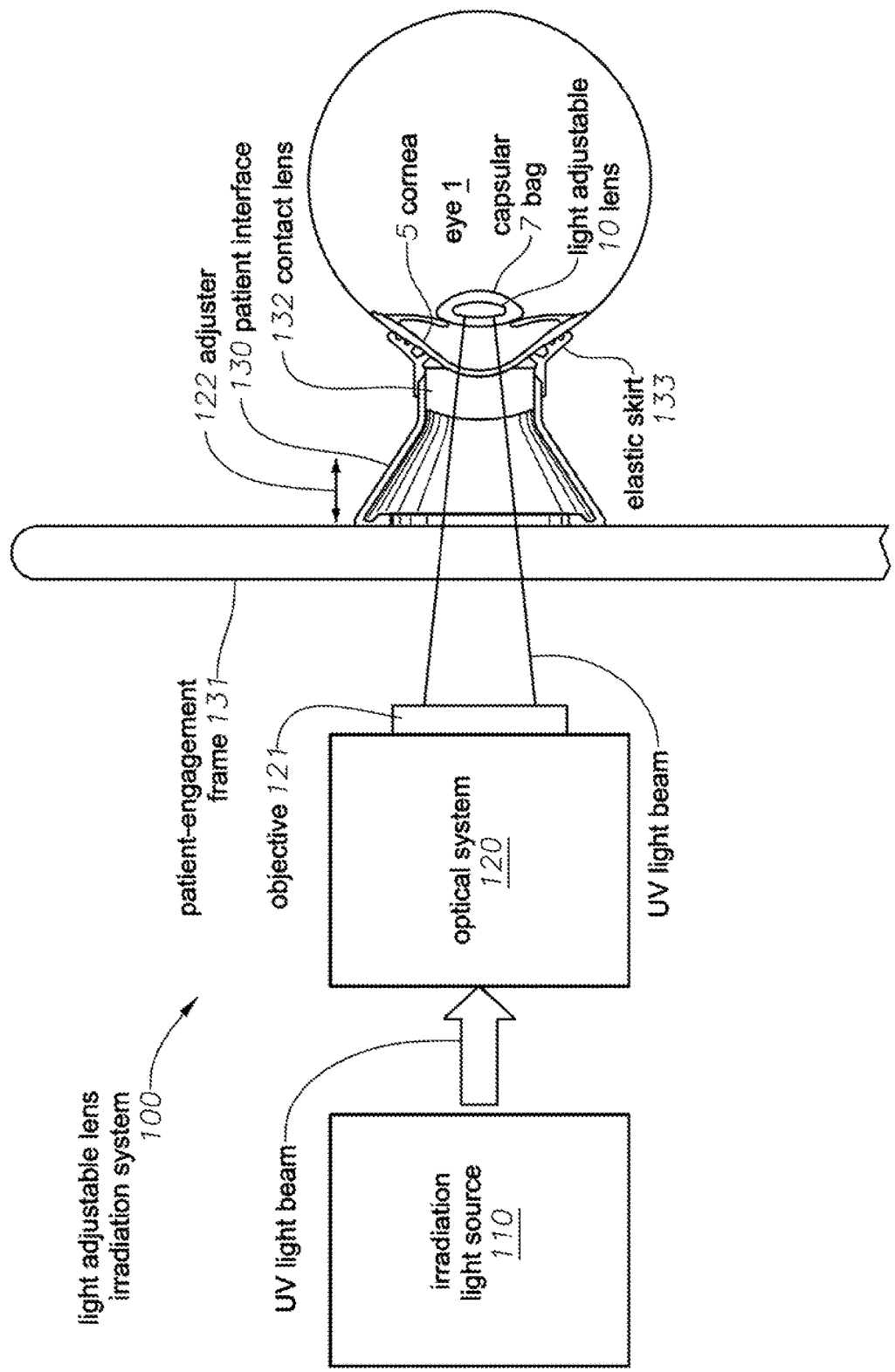
Figure 3C:
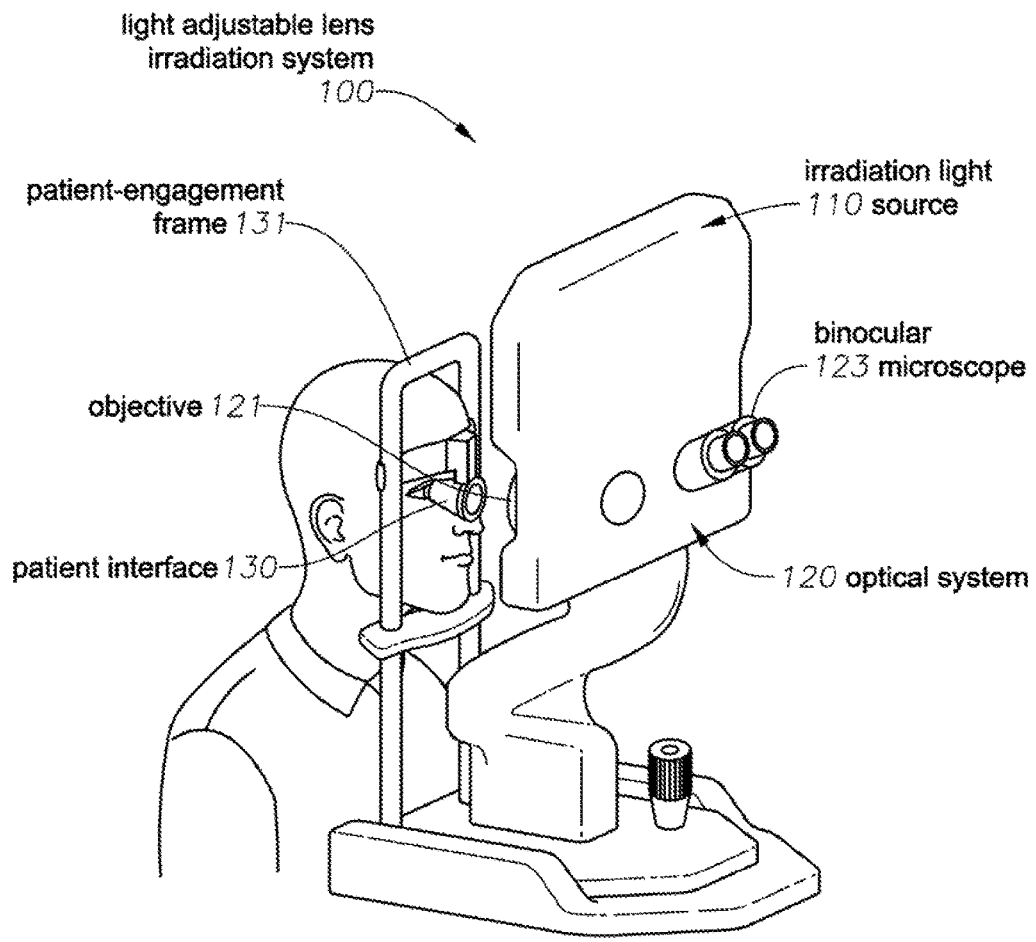

FIGS. 3A-C illustrate a related embodiment of the light adjustable lens irradiation system 100. This LAL irradiation system 100 is largely analogous to the embodiment in FIGS. 2A-C. A difference is that the patient interface 130 is coupled, or affixed, to the patient-engagement frame 131, instead of the optical system 120. In some embodiments, after the patient's head has been immobilized by the patient-engagement frame 131, the adjuster 122 can advance the patient interface 130 to dock with the eye 1 of the patient. Such embodiments immobilize the head of the patient with the patient-engagement frame 131, and the eye 1 and the LAL 10 in it with the patient interface 130. Since the patient-engagement frame 131 shares a rigid base with the optical system 120, immobilizing and stabilizing the light adjustable lens 10 relative to the patient-engagement frame 131 also stabilizes the light adjustable lens 10 relative to the optical system 120. Therefore, such embodiments also enable the high precision alignment of the UV light beam generated by the optical system 120 with the light adjustable lens 10.

Figure 4:
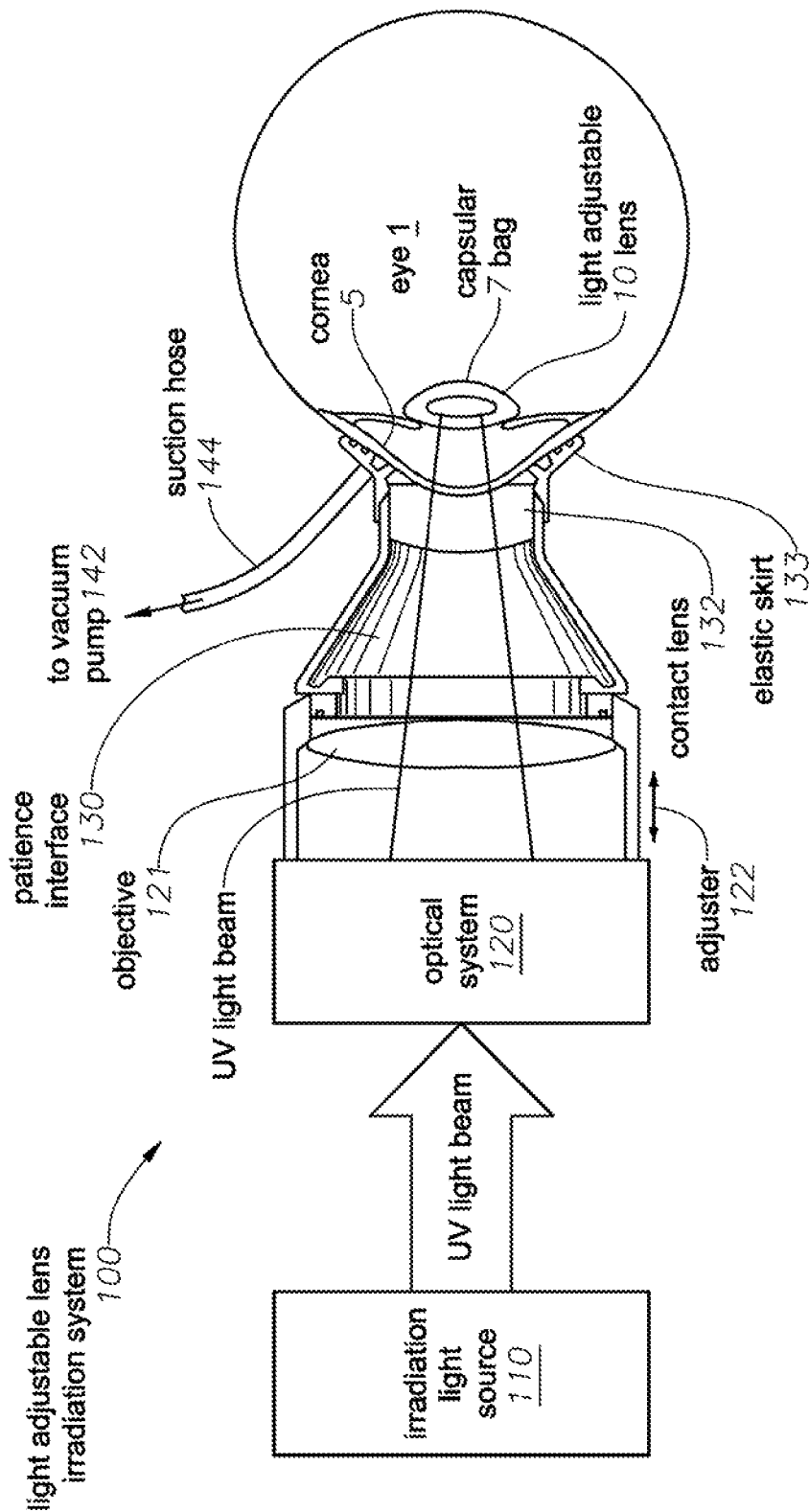
FIG. 4 illustrates a patient interface with vacuum suction.

FIG. 4 illustrates that the strength of the coupling and the mechanical connection between the patient interface 130 and the eye 1 can be increased by including into the LAL irradiation system 100 a vacuum pump 142 for creating vacuum suction; and a suction hose 144, for coupling the vacuum pump 142 to the patient interface 130, in order to transfer the vacuum suction via a fluid connection. The patient interface 130 can include the elastic skirt 133, circularly positioned on a perimeter of the patient interface 130, for applying the vacuum suction to the eye 1 via one or more circular and concentric grooves to stabilize the eye 1. These grooves can distribute the vacuum suction evenly around a ring, to generate a circularly distributed force to hold the eye 1 and the patient interface 130 together efficiently, thereby immobilizing the eye 1.

In other embodiments, the patient interface 130 can include a mechanical engagement portion, for enhancing a mechanical engagement force on the eye 1. The mechanical engagement portion can include protrusions, sharpened edges, tightening members, or enhanced friction members. These protrusions, or edges, concentrate the force to small targeted regions of the cornea 5, or the more peripheral sclera. These protrusions may reversibly indent the cornea 5 and thereby increase the stabilization and immobilization of the eye 1.

In some embodiments of the light adjustable lens irradiation system 100, the patient interface 130 can be a one-piece patient interface 130. Such one-piece patient interfaces 130 can be coupled both to the optical system 120 and to the eye 1 of the patient. However, in practice, doctors sometimes find it challenging to align the eye 1 with a one-piece patient interface 130 in a single step for docking. Patients sometimes react instinctively as the patient interface is moved toward their eye. It can be challenging for the doctors to move the patient interface 130 in response to a moving eye, as the adjuster 122 may be able to adjust the position of the patient interface 130 only in a limited range. Also, the surface of the eye 1 is slippery, and may rotate away while the docking is attempted. Such reactions can result in a failed docking, or an off-center, misaligned docking. Sometimes doctors may have to make multiple attempts to successfully dock the patient interface 130, which can lead to frustration by all involved.

Figure 5A:
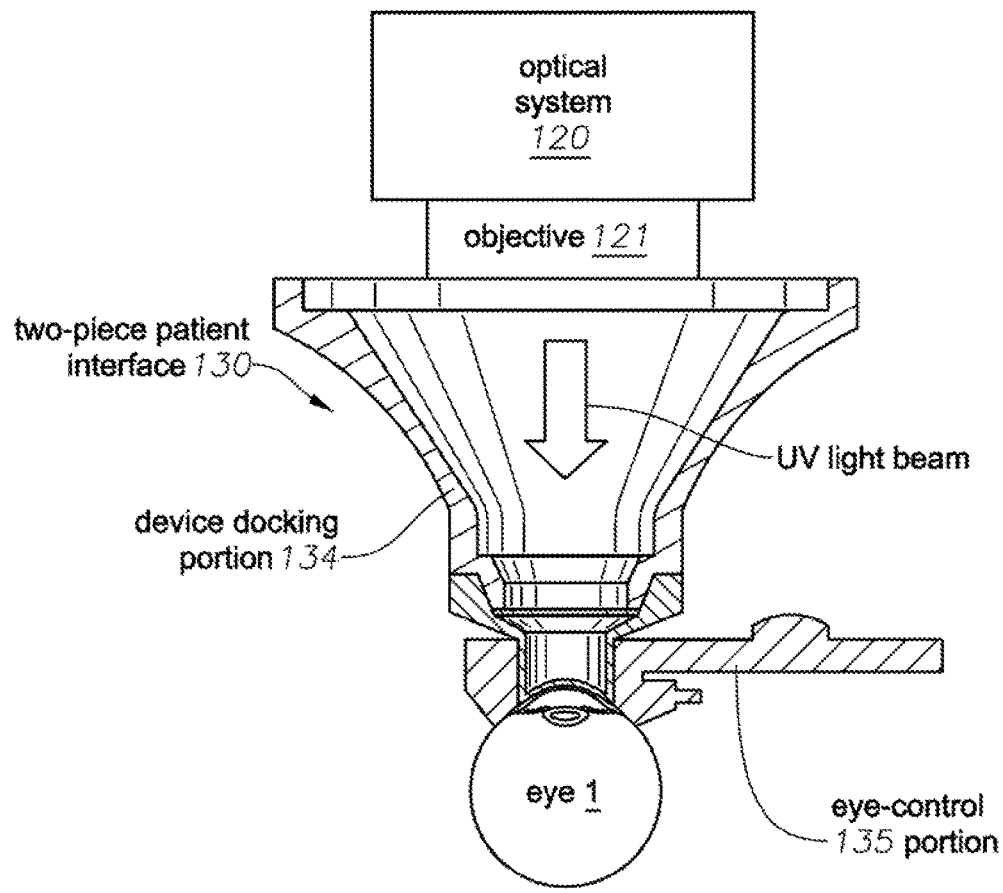
FIGS. 5A-B illustrate a two-piece patient interface.
Figure 5B:
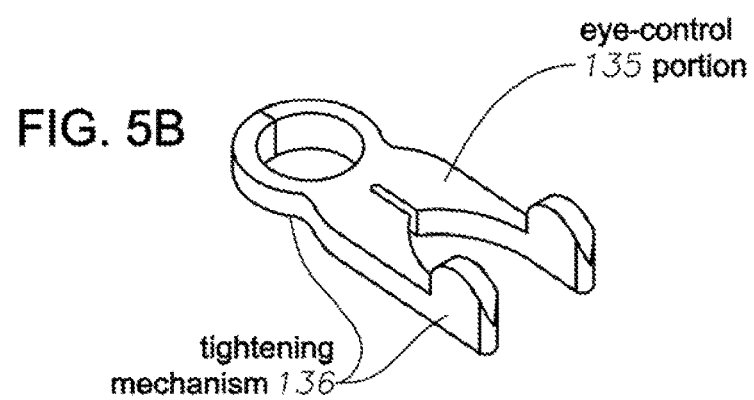

FIGS. 5A-B illustrate a two-piece embodiment of the patient interface 130 that can improve the success rate of the docking. The shown two-piece patient interface 130 breaks the docking into two stages. This two-piece patient interface 130 can include a device docking portion 134, configured to couple to the optical system 120, and an eye-control portion 135, configured to couple to the eye 1 of the patient. The device docking portion 134 and the eye-control portion 135 can be configured to be coupled together to form the full two-piece patient interface 130.

In practice, the doctor can first attach the device docking portion 134 to the distal end of the optical system 120, for example, to its objective 121. Then, the doctor can subsequently and independently maneuver the eye-control portion 135 to align and to dock with the eye 1. Since the eye-control portion 135 is not coupled to the optical system 120, these maneuvers can be performed freely, in a much wider range than the adjuster 122 can adjust the position of a one-piece patient interface 130. Therefore, the success rate of docking the eye-control portion 135 can be very high.

After the docking to the eye 1, the doctor can move the docked eye-control portion 135 slowly towards the device docking portion 134. When done with sufficient care, the docking connection with the eye 1 can be maintained, thereby slowly aligning the eye 1, and the light adjustable lens 10 within, with the device docking portion 134 at the optical system 120. Finally, when the eye-control portion 135 is well-aligned with the device docking portion 134, the two portions can be docked, or coupled with each other to form the full patient interface 130.

In some embodiments, the eye-control portion 135 can include the vacuum suction-enhanced embodiment of FIG. 4. Once the eye-control portion 135 is docked to the eye 1, the vacuum suction can be activated, in order to increase the docking force that holds together the eye-control portion 135 and the eye 1. While sterilization requirements may prefer a disposable device docking portion 134, in some embodiments, the device docking portion 134 may be a permanent part of the optical system 120.

FIG. 5B illustrates that in some other embodiments, the eye-control portion 135 can include a tightening mechanism 136, for an operator to tighten a mechanical coupling with the eye 1 after an initial contact has been established between the eye-control portion 135 of the patient interface 130 and the eye 1. The tightening mechanism 136 can be any one of a variety of options. For example, it can include forceps-like claws, actuated by finger-operated handles, as shown. The doctor can exert force by the finger-operated handles that press, or tighten, the tightening mechanism 136 onto the eye.

Figure 6:
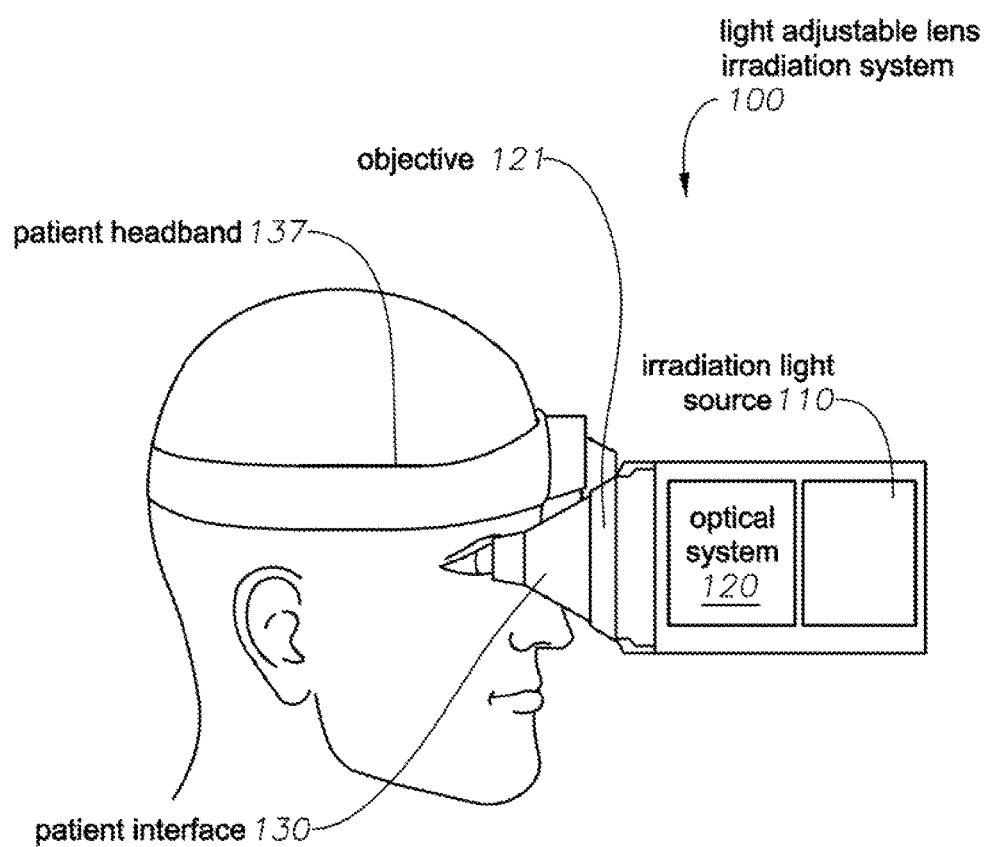
FIG. 6 illustrates a wearable embodiment of the light adjustable lens irradiation system.

FIG. 6 illustrates that some embodiments of the light adjustable lens irradiation system 100 can be remarkably compact. A key controller of such compactification is the possibility of eliminating the binocular microscope 123 as a full-size microscope, since the size of this binocular microscope 123 is an important factor forcing the form factor and scale of the overall LAL irradiation system 100 to be substantial. If, for example, in an embodiment the function of the binocular microscope 123 is performed by a separate digital camera and display, that camera can be miniaturized greatly, allowing the downsizing of the entire LAL irradiation system 100 by a large factor.

In such embodiments, the irradiation light source 110, the optical system 120, and the patient interface 130 can be combined into the shown wearable LAL irradiation system 100. Such wearable LAL irradiation systems 100 can include a patient headband 137, to stabilize the wearable LAL irradiation system 100 relative to a head of a patient.

While this document contains many specifics, details and numerical ranges, these should not be construed as limitations of the scope of the invention and of the claims, but, rather, as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to another subcombination or a variation of a subcombinations.

The invention claimed is:

1. A light adjustable lens irradiation system for post-operatively adjusting optical characteristics of a light adjustable intraocular lens (IOL) in a human eye, the light adjustable lens irradiation system comprising:
   an irradiation light source, for generating an ultraviolet (UV) light beam;
   an optical system, for directing the UV light beam towards a light adjustable intraocular lens, implanted into an eye of a patient; and
   a patient interface, coupled to the optical system, for stabilizing the eye relative to the optical system to achieve an alignment of the light adjustable intraocular lens and the UV light beam,
   wherein the patient interface is sized and configured to directly couple to the eye of the patient,
   wherein the optical system includes an objective, and the patient interface and the objective are spatially separated, wherein the objective is laterally adjustable relative to the patient interface, wherein the optical system directs the UV light beam to irradiate a central portion of the intraocular lens, and wherein the optical system modulates the UV light beam to attain a radial intensity profile, wherein the light adjustable intraocular lens is fabricated from photo-polymerizable macromers, interspersed with a photoinitiator, wherein the radial intensity profile of the irradiating UV light induces polymerization of the photo-polymerizable macromers with a corresponding radial profile, and wherein polymerizing with a radial profile changes the shape of the light adjustable intraocular lens, and therefore changes the optical characteristics of the light adjustable intraocular lens.

2. The light adjustable lens irradiation system of claim 1, comprising:
   a patient-engagement frame, for engaging a head of the patient;
   wherein the patient interface is coupled to the patient-engagement frame.

3. The light adjustable lens irradiation system of claim 1, comprising:
   a vacuum pump; for creating vacuum suction; and
   a suction hose, for coupling the vacuum pump to the patient interface to transfer the vacuum suction via a fluid connection,
   wherein the patient interface includes an elastic skirt, circularly positioned on a perimeter of the patient interface, for applying the vacuum suction to the eye to stabilize the eye.

4. The light adjustable lens irradiation system of claim 1, the patient interface comprising:
   a mechanical engagement portion, for enhancing a mechanical engagement force on the eye, by including at least one of protrusions, sharpened edges, tightening members, and enhanced friction members.

5. The light adjustable lens irradiation system of claim 1, wherein:
   the patient interface is a one-piece patient interface, for coupling both to the optical system and to the eye of the patient.

6. The light adjustable lens irradiation system of claim 1, wherein:
   the patient interface is a two-piece patient interface, including a device docking portion, configured to couple to the optical system, and
   an eye-control portion, configured to couple to the eye of the patient; wherein the device docking portion and the eye-control portion are configured to be coupled together.

7. The light adjustable lens irradiation system of claim 6, the eye-control portion comprising:
   a tightening mechanism, for an operator to tighten a mechanical coupling with the eye after an initial contact has been established between the eye-control portion of the patient interface and the eye.

8. The light adjustable lens irradiation system of claim 1, wherein:
   the irradiation light source, the optical system, and the patient interface are combined into a wearable light adjustable lens irradiation system.

9. The light adjustable lens irradiation system of claim 8, comprising:
   a headband, to stabilize the wearable light adjustable lens irradiation system relative to a head of a patient.

10. The light adjustable lens irradiation system of claim 1, the optical system comprising:
   a digital mirror device, for directing the UV light beam towards the eye, and for modulating the UV light beam to attain said radial intensity profile.

* * * * *